United States Patent
Kim et al.

(10) Patent No.: US 9,980,953 B2
(45) Date of Patent: May 29, 2018

(54) COMBINED COMPOSITION FOR PREVENTING OR TREATING CANCER COMPRISING A BENZOPHENONE THIAZOLE DERIVATIVES AS A VDA AND TOPOISOMERASE INHIBITOR

(71) Applicants: CHONG KUN DANG PHARMACEUTICAL CORP., Seoul (KR); NATIONAL CANCER CENTER, Goyang-si OT (KR)

(72) Inventors: Soo Jin Kim, Yongin-si (KR); Young Sang Kim, Goyang-si (KR); MinChae Kim, Seoul (KR); Young-Whan Park, Goyang-si (KR); Jung-Yong Kim, Goyang-si (KR); In Chull Kim, Goyang-si (KR)

(73) Assignees: CHONG KUN DANG PHARMACEUTICAL CORP., Seoul (KR); NATIONAL CANCER CENTER, Goyang-si (KR)

( * ) Notice: Subject to any disclaimer, the term of this patent is extended or adjusted under 35 U.S.C. 154(b) by 0 days. days.

(21) Appl. No.: 15/447,247

(22) Filed: Mar. 2, 2017

(65) Prior Publication Data
US 2018/0085363 A1    Mar. 29, 2018

Related U.S. Application Data

(60) Provisional application No. 62/400,054, filed on Sep. 26, 2016.

(51) Int. Cl.
| A61K 31/497 | (2006.01) |
| A61K 31/4545 | (2006.01) |
| A61K 31/427 | (2006.01) |
| A61K 9/00 | (2006.01) |

(52) U.S. Cl.
CPC ........ *A61K 31/4545* (2013.01); *A61K 9/0019* (2013.01); *A61K 9/0053* (2013.01); *A61K 31/427* (2013.01)

(58) Field of Classification Search
CPC .................................................. A61K 31/4545
USPC ............................................ 514/253, 253.02
See application file for complete search history.

(56) References Cited

U.S. PATENT DOCUMENTS

| 4,604,463 A * | 8/1986 | Miyasaka | ............ | C07D 491/22 |
| | | | | 544/125 |
| 8,362,267 B2 * | 1/2013 | Choi | .................... | C07D 417/10 |
| | | | | 548/190 |
| 2009/0275575 A1 | 11/2009 | Choi et al. | | |
| 2011/0021582 A1 | 1/2011 | Choi et al. | | |

FOREIGN PATENT DOCUMENTS

| WO | 2004-091620 | 10/2004 |
| WO | 2005-117877 | 12/2005 |
| WO | 2009-073869 | 6/2009 |
| WO | 2009-119980 | 10/2009 |

OTHER PUBLICATIONS

Abdel-Aziz W, et al., "An in vitro model system that can differentiate the stages of DNA replication affected by anticancer agents", Biochemical Pharmacology, vol. 68, No. 1, Jul. 1, 2004, pp. 11-21.
Hsiang YH, et al., "Identification of mammalian DNA topoisomerase I as an intracellular target of the anticancer drug camptothecin", Cancer Research vol. 48, No. 7, Apr. 1988, pp. 1722-1726.
Jong Cheol Lee et al., "Arsenic Trioxide as a Vascular Disrupting Agent: Synergistic Effect with Irinotecan on Tumor Growth Delay in a CT26 Allograft Model", Translational oncology, 6 (1), pp. 83-91, Feb. 2013.
G. Kenneth Lloyd et al., "A New Vascular/Tubulin Modifying Agent Greatly Potentiates Standard Chemotherapy in Xenograft Models", AACR, Jul. 2003.
Chang Hoon Moon et al., "KML001 Displays Vascular Disrupting Properties and Irinotecan Combined Antitumor Activities in Murine Tumor Model", PLoS ONE, 8(1), e53900, Jan. 2013.
KIPO, International Search Report, Application No. of PCT/KR2017/009889, dated Dec. 13, 2017.
KIPO, Written Opinion of the International Searching Authority, Application No. of PCT/KR2017/009889, dated Dec. 13, 2017.

* cited by examiner

*Primary Examiner* — Kevin E Weddington
(74) *Attorney, Agent, or Firm* — Lex IP Meister, PLLC

(57) ABSTRACT

The present invention relates to a pharmaceutical combined composition for preventing or treating cancer comprising a compound of formula 1 or a pharmaceutically acceptable salt thereof and topoisomerase inhibitor as active ingredients. The pharmaceutical combined composition of the present invention specifically inhibits cell proliferation and induces apoptosis as to various cancers such as colorectal cancer and ovarian cancer that a vascular disrupting agent cannot treat due to a complex inhibition mechanism of neoplasm of the compound of formula 1 and the pharmaceutically acceptable salt thereof and topoisomerase inhibitor, and thereby it can be usefully used for preventing and treating cancer.

11 Claims, 2 Drawing Sheets

(CR: Complete reponse, PR: Partial response)

COMBINED COMPOSITION FOR PREVENTING OR TREATING CANCER COMPRISING A BENZOPHENONE THIAZOLE DERIVATIVES AS A VDA AND TOPOISOMERASE INHIBITOR

CROSS REFERENCE TO RELATED APPLICATION

This application claims the benefit of U.S. Provisional Application Ser. No. 62/400,054, filed on Sep. 26, 2016, the contents of which are incorporated by reference herein in their entireties.

TECHNICAL FIELD

The present invention relates to a pharmaceutical composition comprising 2 kinds of active ingredients that are useful for treating neoplastic diseases, and more particularly to a pharmaceutical combined composition comprising a vascular disrupting agent (hereinafter referred to as 'VDA') and a topoisomerase inhibitor-based chemical toxic agent as active ingredients.

BACKGROUND ART

Cancer is a serious threat in public health. The growth of malignant cancer is a serious challenge to a modern medical science due to its unique characteristics. These characteristics of cancer include uncontrolled cell proliferation causing loss of growth control exhibited by malignant tissues, capability for invading even local and distal tissues, unregulated cell differentiation, and often absence of effective treatment and prevention. Although cancer can develop in virtually any of the body's tissue at any stage, its etiology has not been completely explained. At present, a part of available major therapeutic methods are a surgery, radiotherapy and chemotherapy. The surgery often can be extreme means and cause serious results. The radiotherapy has an advantage of killing cancer cells, but this also damages non-cancer tissues simultaneously. The chemotherapy includes administering various anti-cancer drugs to a patient, but this often accompanies harmful side-effects. Globally, more than ten millions of people are diagnosed with cancer every year, and that number is predicted to increase to fifteen millions of new cases every year by 2020.

Of this chemotherapy, currently widely used three S phase of cell cycle-specific anti-cancer agents, 1-β-Darabinofuranosylcytosine (ara-C), camptothecin (CPT) and doxorubicin (DOX) are targeting three different enzymes (DNA polymerase α, topoisomerase I and II) (Abdel-Aziz W, et al., Biochem. Pharmacol., 68, pp 11-21, 2004). In some researches, topoisomerae I has been identified as a target molecule of camptothecin kind such as topotecan and irinotecan, etc (Hsiang Y H, et al., Cancer Res., 48, pp 1722-1726, 1988). Topoisomerase is classified to two kinds according to a cutting method of DNA strands. Type I topoisomerase (topoisomerase I) changes the status of DNA after making single-strand nick be formed in DNA substrates instantaneously, and Type II topoisomerase (topoisomerase II) changes the status of DNA after cutting all of DNA double-strands.

Furthermore, a vascular disrupting agent (VDA) is a drug which works in tumor vascular endothelial cells and decrease blood flow rate of a tumor blood vessels. Up to now many VDAs have been developed, but they are not developed for treating colorectal cancer or gastric cancer among cancers and there is not any drug having excellent effects on those cancers.

In addition, it is suggested that the efficacy of VDA can be significantly improved when it is administered by combining more than one therapy which has different mechanism from VDA in the aspect of coadministration, but until now there is no successful case. Therefore, the requirement for developing combination therapy and formulations composed of VDA and other therapy, thereby having relatively low toxicity and excellent effects on preventing or treating cancers such as colorectal cancer or ovarian cancer has been increased.

Technical Solution

Under these circumstances, the present inventors have repeatedly studied combination therapies and formulations having effects on preventing or treating cancer, which is improved by combining a vascular disrupting agent (VDA) and anti-cancer agents of other mechanism, and in result, they have demonstrated that a synergistic anti-cancer effect can be secured in various cancer, particularly colorectal cancer or ovarian cancer where a vascular disrupting agent is not applicable in the past, because in case of combining a compound of formula 1 as a vascular disrupting agent and topoisomerase inhibitor, an anti-cancer combined composition having an excellent effect on preventing or treating cancer can be obtained, thereby completing the present invention.

Thus, the object of the present invention is to provide a combined composition for preventing or treating cancer comprising a compound of the following formula 1 and topoisomerase inhibitor as a vascular disrupting agent (VDA).

DISCLOSURE OF INVENTION

Technical Problem

As an aspect to achieve the above object, the present invention relates to a pharmaceutical combined composition for preventing or treating cancer comprising (1) the first active ingredient of (S)-N-(4-(3-(1H-1,2,4-triazol-1-yl) -4-(3,4,5-trimethoxybenzoyl)phenyl)thiazol-2-yl)-2-amino-3-methylbutanamide, which is a derivative of benzophenone thiazole and is represented as formula 1, or its pharmaceutically acceptable salt and (2) the second active ingredient of topoisomerase.

[Formula 1]

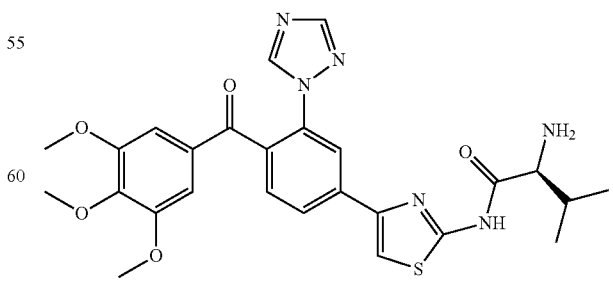

Hereinafter, the present invention will be explained in detail.

The first active ingredient of the pharmaceutical combined composition according to the present invention is a compound of the above formula 1, and the compound has activity as a vascular disrupting agent (VDA). The explanation and preparation method as to the compound of formula 1 is described in detail in International Patent Publication WO 2009-119980, and that is included as a reference to the present invention. In the present invention the compound of formula 1 can be prepared by the method disclosed in the above literature. Generally, the dosage of the compound of formula 1 administered to human varies with various administration factors including a factor which is specific to an individual patient, but it is known that 1 to 12 mg/m$^2$ is administered in case of intravenous administration and 2.5 to 20 mg is administered in case of oral administration.

Meanwhile, the second active ingredient of the pharmaceutical combined composition according to the present invention is a topoisomerase inhibitor, and DNA topoisomerase is an essential enzyme for DNA relaxation during numerous important processes including replication, transcription and repair. The topoisomerase inhibitor is a drug which is designed to inhibit topoisomerase enzymes (topoisomerase I and/or II), which is an enzyme regulating DNA structural change by cut the phosphate backbone of DNA strands and ligation during cell cycle. It is considered that the topoisomerase inhibitor blocks a ligation step, thereby occurring single and/or double strand breakage that harms completeness of genome. Specifically, the topoisomerase inhibitor comprised in the pharmaceutical composition of the present invention may be topotecan, irinotecan, lurtotecan, exatecan, pyridobenzoindole, and pharmaceutically acceptable salts thereof, and preferably, irinotecan represented by the following formula 2 or its pharmaceutically acceptable salt.

[Formula 2]

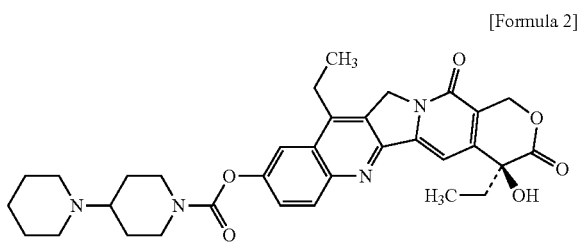 [SMILES: CCc1c2c(nc3ccc(OC(=O)N4CCC(N5CCCCC5)CC4)cc13)-c1cc3c(c(=O)n1C2)COC(=O)[C@]3(O)CC]

Irinotecan is a topoisomerase I inhibitor, and chemically a semisynthetic derivative of a natural alkaloid, camptotecin, and it changes to an active metabolite called SN-38 by hydrolysis.

In the present invention, the pharmaceutically acceptable salt means salts commonly used in the medical industry, for example, inorganicionic salts prepared by calcium, potassium, sodium and magnesium, etc., inorganic acid salts prepared by hydrochloric acid, nitric acid, phosphoric acid, bromic acid, iodic acid, perchloric acid, tartaric acid, and sulfuric acid, etc., organic acid salts prepared by acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc., sulfornates prepared by methane sulfonic acid, ethane sulfonic acid, benzene sulfonic acid, p-toluene sulfonic acid, and naphthalene sulfonic acid, etc, amino acid salts prepared by glycine, arginine, lysine, etc., and amine salts prepared by trimethylamine, triethylamine, ammonia, pyridine, picoline, etc., and so on, but the kind of salts of the present invention is not limited to those listed salts.

According to one example embodiment of the present invention, the first active ingredient may be a hydrochloride of (S)-N-(4-(3-(1H-1,2,4-triazol-1-yl) -4-(3,4,5-trimethoxybenzoyl)phenyl)thiazol-2-yl)-2-amino-3-methylbutanamide (the compound of formula 1), and the second active ingredient may be irinotecan hydrochloride.

In one specific embodiment, the first active ingredient and the second active ingredient may be included in an amount of 1.4 to 16.7 parts of weight (the first active ingredient) and 83.3 to 98.6 parts of weight (the second active ingredient), respectively, per 100 parts by weight of the total combined composition. In addition, the content ratio of the first active ingredient and the second active ingredient is 1:5 to 1:70.

The pharmaceutical combined composition of the present invention may comprise the first active ingredient and the second active ingredient separately as two kinds of unit administration form or one combined unit administration form.

The pharmaceutical combined composition of the present invention may be administered by various administration manners according to an objected method, specifically oral administration or non-oral administration (for example, intravenous, subcutaneous, intraperitoneal, or local administration). In the present invention, in case that the pharmaceutical combined composition comprises two kinds of separate formulations, formulations comprising each active ingredient may be administered by same or different manners. For example, the first active ingredient may be administered non-orally or orally, preferably orally. In addition, the second active ingredient may be administered non-orally.

In the pharmaceutical combined composition of the present invention, an appropriate dosage of the first active ingredient and the second active ingredient may vary according to weight, age, gender, health condition, diet of a patient, administration time, administration manner, emission rate and severity of disease, etc. As one specific example, a daily dosage of the first active ingredient of the present invention is approximately 1 to 20 mg/kg, preferably 2 to 10 mg/kg. In addition, a daily dosage of the second active ingredient of the present invention is approximately 5 to 50 mg/kg, preferably 10 to 30 mg/kg. However, due to characteristics of cancer which is a target disease of the pharmaceutical composition according to the present invention, a dosage of each ingredient may change a lot according to the above conditions, and it is not limited to the above example.

In the pharmaceutical combined composition of the present invention, an appropriate administration period of the first active ingredient and the second active ingredient may be determined according to the above dosage. For example, they may be administered simultaneously, in order (in any order), in combination, for prevention, treatment or prevention of cancer metastasis according to the present invention. For example, the first active ingredient of the present invention may be administered once a day to once a week, preferably once a day. In addition, the second active ingredient of the present invention may be administered once a day to once a week, preferably twice a week.

According to one example embodiment of the present invention, an administration period of the combined composition of the present invention is a week, and the first active ingredient may be administered orally once a day or by injection once a week from the first day to the seventh day and the second active ingredient may be administered twice a week from the first day to the seventh day.

It is demonstrated that the pharmaceutical combined composition according to the present invention has a synergistic and complementary effect of the first active ingredient which is a vascular disrupting agent (VDA) and the second active ingredient which is an angiogenesis inhibitor, thereby having an excellent anti-cancer activity.

Thus, the combined composition for preventing or treating cancer of the present invention may be usefully used as an anti-cancer therapeutic strategy, and particularly, it is preferably for treating solid cancer. The solid cancer may be selected from the group consisting of liver cancer, lung cancer, gastric cancer, kidney cancer, colorectal cancer, pancreatic cancer, prostate cancer, bladder cancer, uterine cancer, ovarian cancer, breast cancer and thyroid cancer, preferably colorectal cancer or ovarian cancer.

According to the example embodiment of the present invention, the colorectal cancer may be a primary colorectal cancer.

In the present invention, the first active ingredient and the second active ingredient comprised in the pharmaceutical combined composition of the present invention may be comprised in a separate pharmaceutical composition respectively, and the pharmaceutical composition may be prepared as a unit capacity form by formulating using a pharmaceutically acceptable carrier or prepared by injecting to a high-capacity container, according to a method that a person having ordinary skill in the art to which this invention belongs can easily implement.

The pharmaceutically acceptable carrier is commonly used during formulating and includes lactose, dextrose, sucrose, sorbitol, mannitol, starch, acacia gum, calcium phosphate, arginate, gelatin, calcium silicate, microcrystalline cellulose, polyvinylpyrrolidone, cellulose, water, syrup, methyl cellulose, methyl hydroxybenzoate, propylhydroxybenzoate, talc, magnesium stearate and mineral oil, etc., but is not limited to. The pharmaceutical composition of the present invention may additionally comprise lubricants, humectants, sweetening agents, flavoring agents, emulsifiers, suspensions, preservatives, etc. The appropriate pharmaceutically acceptable carriers and formulations have been described in Remington's Pharmaceutical Sciences (19th ed., 1995)

The present invention provides a method for preventing or treating cancer comprising administering a pharmaceutical combined composition according to the present invention to a needy subject. In the present invention, the term "subject" includes mammals, particularly human, and administration plan, administration gap, dosage, etc. may be easily established, altered, and controlled by a person skilled in the art by the aforementioned factors.

Advantageous Effects

The combined composition of the present invention has an synergistic effect of preventing or treating cancer, which is excellent in cancer, specifically in solid cancer such as colorectal cancer or ovarian cancer, by specially combining the first active ingredient that is a vascular disrupting agent (VDA) and the second active ingredient that is topoisomerase inhibitor, and thereby it is very useful as an anticancer agent.

BEST MODE FOR CARRYING OUT THE INVENTION

Figure 1A:
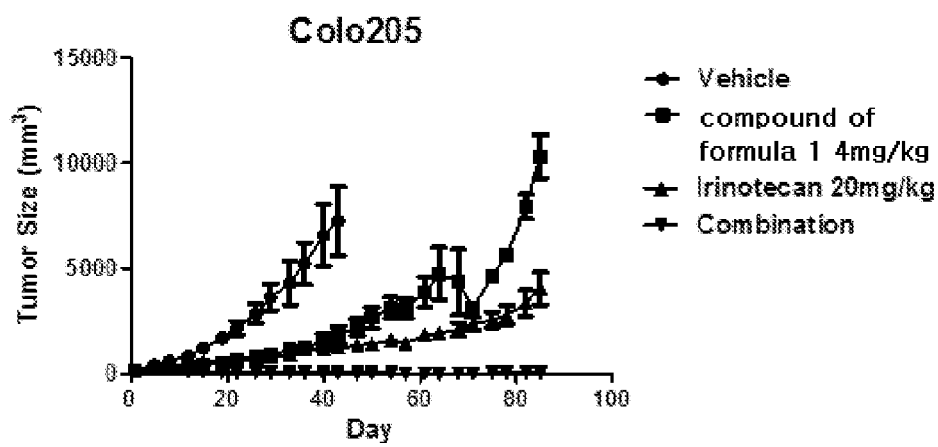
FIG. 1a is a graph of cancer growth of control group and each experimental groups in a Colo205 xenograft mouse model. In the experiment, the compound of formula 1 is orally administered.
Figure 1B:
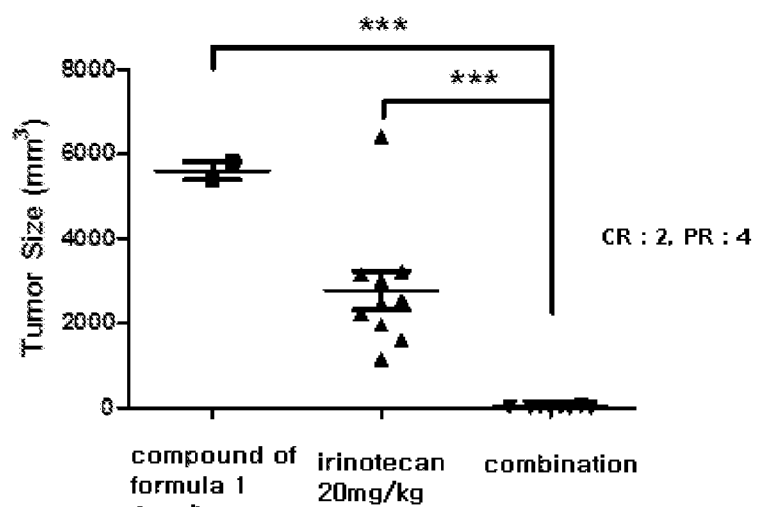
FIG. 1b is a graph of tumor size of each subject at day 78 of the experiment in a Colo205 xenograft mouse model. Vehicle group is not included in the graph because cancer was so large that experimental animals were euthanized at day 43.
Figure 2A:
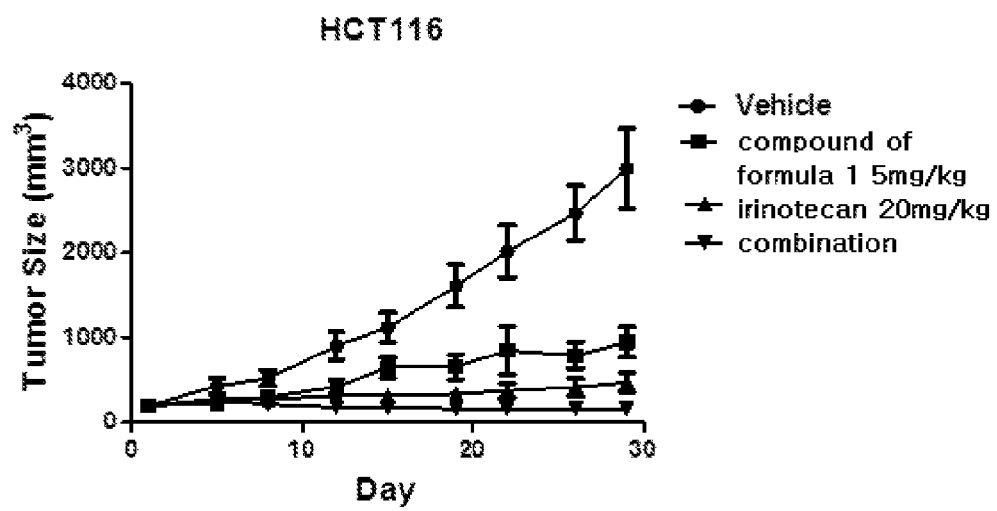
FIG. 2a is a graph of cancer growth of vehicle group and each experimental group in a HCT116 xenograft mouse model. In the experiment, the compound of formula 1 is intraperitoneally administered.
Figure 2B:
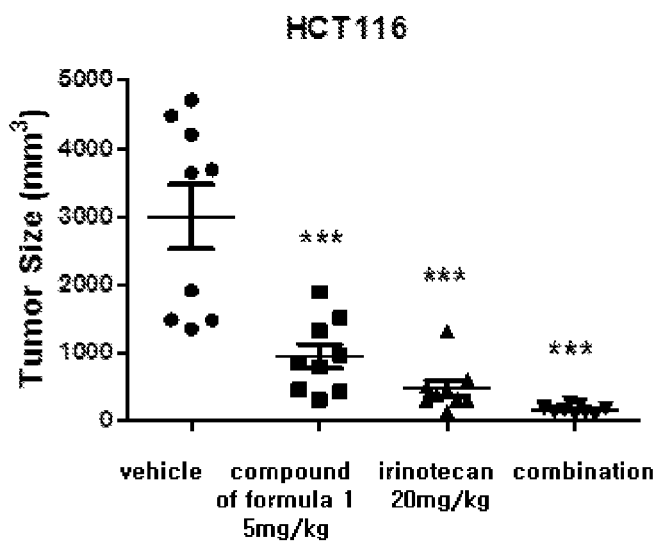
FIG. 2b is a graph of tumor size of each subject at day 29 of the experiment in a HCT116 xenograft mouse model.

Hereinafter, the configuration and effect of the present invention will be described in further detail with examples. These examples are illustrative purposes only and the scope of the present invention is not limited by these examples.

Example 1: Demonstration of Anti-Cancer Effect of the Combined Composition According to the Present Invention in a Colo205 Xenograft Mouse Model 1-1) Experimental Method
a. Preparation of Animal Tumor Model A human colorectal cancer cell line, Colo205 was purchased from ATCC (USA). The Colo205 cell line was maintained with RPMI1640 (Gibco, USA) including 10% fetal bovine serum (FBS; Gibco, Grand Island, N.Y., USA) and 1% antibiotics (Gibco, USA).

The human colorectal carcinoma, Colo205 cell was subcutaneously administered in BALB/c-nu/nu male mice ($5 \times 10^6$ cell/head), and after grouping in order to making an average size of tumor 165~167 $mm^3$, used in experiments.

b. Preparation of Active Ingredients

A compound of formula 1 was prepared by the preparation method disclosed in International Laid-open Patent Publication WO 2009-119980, and prepared at 0.4 mg/ml concentration by dissolving with distilled water.

Irinotecan (Boryung, Korea) was prepared at 2 mg/ml concentration by diluting with 5% glucose saline solution. The solution to be used was prepared on the day of use, and remained solution was discarded.

c. Demonstration of Anti-Tumor Activity

The anti-cancer effect of the compound of formula 1 and irinotecan was estimated in the Colo205 xenograft model. Experimental groups were divided into the following administration groups.

Control group: vehicle

Single administration group of the compound of formula 1: the compound of formula 1 (4 mg/kg, every day, oral)

Single administration group of irinotecan: irinotecan (20 mg/kg, once per 4 days, injection)

Coadministration group: the compound of formula 1 (4 mg/kg, every day, oral), irinotecan (20 mg/kg, once per 4 days, injection)

All the experimental groups were orally and intraperitoneally administered for 10 weeks. Toxicity was observed by measuring weight of mice, and the growth of tumor was measured using calipers during experimental period. The volume of tumor was calculated according to the following calculation formula.

$$\text{tumor volume} = (\text{length} \times \text{width}^2)/2$$

d. Statistical Analysis

The data of size of tumor, regression of tumor, and body weight changes was tested using Bartlett's test at significance level α=0.05, and as a result of the test, data having no significance was tested using one-way analysis of variance at significance level α=0.05, and data having significance was tested using Kruskal-Wallis test at significance level α=0.05.

Statistical analysis between each group was performed using GraphPad PRISM® Version 5.0 (GraphPad Software, USA).

1-2) Experimental Results—Anti-Cancer Activity of the Compound of Formula 1 in a Colo205 Xenograft Model In order to estimate anti-tumor effect by coadministration of oral administration of the compound of formula 1 and injection of irinotecan, each material was administered to xenograft mice, and weight and growth of tumor were observed for 85 days. Vehicle administration group was euthanized at the day 43 because cancer became too big.

In coadministration group of the compound of formula 1 and irinotecan, emaciation, etc. was observed to 1 mouse at 6th day and 44th day, respectively, and then it was dead. In single administration group of the compound of formula 1, 8 mice were dead, and fighting evidence between subjects was observed in 3 mice among death discovered subjects, and symptoms such as emaciation, etc. were observed in the other 5 mice. There was no dead subject in vehicle administration group and single administration group of irinotecan.

In an aspect of inhibitory effect of growth of tumor, the size of tumor of administration group of the compound of formula 1 and administration group of irinotecan was significantly decreased compared to administration group of an excipient during administration period. Particularly, degree of decrease of size of tumor was the biggest in coadministration group of the compound of formula 1 and irinotecan, and complete remission was observed in 2 mice among 10 mice at the 78th day after administration, and partial remission was observed in 4 mice.

These results suggest that anti-cancer effect of coadministration of the compound of formula 1 and irinotecan is very great.

Example 2: Demonstration of Anti-Cancer Effect of the Combined Composition According to the Present Invention in a HCT116 Xenograft Mouse Model 2-1) Experimental Method
a. Preparation of Animal Tumor Model A human colorectal cancer cell line, HCT116 was purchased from ATCC (USA). The HCT116 cell line was maintained with RPMI1640 (Gibco, USA) including 10% fetal bovine serum (FBS; Gibco, USA).

The human colorectal carcinoma, HCT116 cell was subcutaneously administered in Athymic nude mouse (Hsd: Athymic Nude-Foxn1$^{nu}$) male mice (5×10$^6$ cell/head), and used in experiments when the size of tumor became 150-200 mm$^3$.

b. Preparation of Active Ingredients

A compound of formula 1 was prepared by the preparation method disclosed in International Laid-open Patent Publication WO 2009-119980, and prepared at 0.5 mg/ml concentration by dissolving with 0.9% saline solution.

Irinotecan (Jeilpharm, Korea) was prepared at 2 mg/ml concentration by diluting with 5% dextrose solution.

The solution to be used was prepared on the day of use, and remained solution was discarded.

c. Demonstration of Anti-Tumor Activity

The anti-cancer effect of the compound of formula 1 and irinotecan was estimated in the HCT116 xenograft model. Experimental groups were divided into the following administration groups.

Control group: vehicle
Single administration group of the compound of formula 1: the compound of formula 1 (5 mg/kg, once a week, injection)
Single administration group of irinotecan: irinotecan (20 mg/kg, once per 4 days, injection)
Coadministration group: the compound of formula 1 (5 mg/kg, once a week, injection), irinotecan (20 mg/kg, once every 4 days, injection)

All the experimental groups were intraperitoneally administered for 4 weeks. Toxicity was observed by measuring weight of mice, and the growth of tumor was measured using calipers during experimental period. The volume of tumor was calculated according to the following calculation formula.

$$\text{tumor volume} = (\text{length} \times \text{width}^2)/2$$

d. Statistical Analysis

The data of size of tumor, regression of tumor, and body weight changes was tested using One-way ANOVA test at significance level α=0.05, and data having significance was tested using Dunnett's multiple comparison test at significance level α=0.05.

Statistical analysis between each group was performed using PRISM® Version 5.03 (GraphPad Software, USA).

2-2) Experimental Results—Anti-Cancer Activity of the Compound of Formula 1 in a HCT116 Xenograft Model In order to estimate anti-tumor effect by coadministration of administration of the compound of formula 1 and irinotecan injection, each material was administered to xenograft mice, and weight and growth of tumor were observed for 4 weeks.

In all groups, death, dying condition, and weight loss were not observed.

In an aspect of inhibitory effect of growth of tumor, the size of tumor of administration group of the compound of formula 1 and administration group of irinotecan was significantly decreased compared to administration group of an excipient during administration period. Particularly, degree of decrease of size of tumor was the biggest in coadministration group of the compound of formula 1 and irinotecan, and partial response was observed in 3 mice.

These results suggest that anti-cancer effect of coadministration of the compound of formula 1 and irinotecan is very great.

The invention claimed is:

1. A pharmaceutical combined composition for treating cancer comprising:
   1) a compound of the following formula 1 as a first active ingredient; and
   2) a topoisomerase inhibitor as a second active ingredient,

[Formula 1]

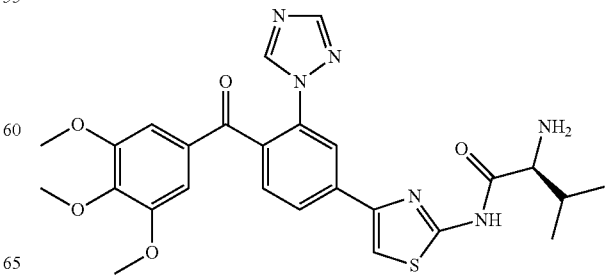

wherein the cancer is solid cancer selected from the group consisting of liver cancer, lung cancer, gastric cancer, kidney cancer, colorectal cancer, pancreatic cancer, prostate cancer, bladder cancer, ovarian cancer, ovarian cancer, breast cancer and thyroid cancer.

2. The combined composition of claim 1, wherein the topoisomerase inhibitor is at least one selected from the group consisting of topotecan, irinotecan, lurtotecan, exatecan, pyridobenzoindole, and pharmaceutically acceptable salts thereof.

3. The combined composition of claim 1, wherein the topoisomerase inhibitor is irinotecan of the following formula 2 or its hydrochloride:

[Formula 2]

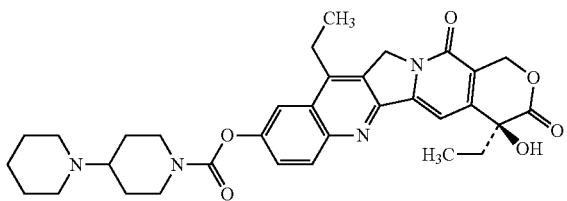

4. The combined composition of claim 1, wherein the first active ingredient is a hydrochloride of the compound of formula 1 (S)-N-(4-(3-(1H-1,2,4-triazol-1-yl) -4-(3,4,5-trimethoxybenzoyl)phenyl)thiazol-2-yl)-2-amino-3-methylbutanamide).

5. The combined composition of claim 1, wherein the first active ingredient and the second active ingredient are in an amount of 1.4 to 16.7 parts of weight and 83.3 to 98.6 parts of weight, respectively, per 100 parts by weight of the total combined composition.

6. The combined composition of claim 1, wherein the solid cancer is colorectal cancer or uterine cancer.

7. The combined composition of claim 1, wherein the first active ingredient and the second active ingredient are comprised in a shape of separate formulations, respectively.

8. The combined composition of claim 1, wherein the first active ingredient and the second active ingredient are combined and comprised in a shape of a single formulation.

9. The combined composition of claim 7, wherein the first active ingredient is comprised as a formulation for oral administration and the second active ingredient is comprised as a formulation for injection.

10. The combined composition of claim 7, wherein a formulation comprising the first active ingredient and a formulation comprising the second active ingredient among the combined composition can be administered simultaneously or sequentially.

11. The combined composition of claim 9, wherein a formulation comprising the first active ingredient and a formulation comprising the second active ingredient among the combined composition can be administered simultaneously or sequentially.

* * * * *

UNITED STATES PATENT AND TRADEMARK OFFICE
CERTIFICATE OF CORRECTION

PATENT NO. : 9,980,953 B2  
APPLICATION NO. : 15/447247  
DATED : May 29, 2018  
INVENTOR(S) : Soo Jin Kim et al.

Page 1 of 1

It is certified that error appears in the above-identified patent and that said Letters Patent is hereby corrected as shown below:

In the Claims  
    Column 9, Line 4, Claim 1    delete "ovarian cancer, ovarian"  
                                          insert -- ovarian cancer, uterine --

Signed and Sealed this  
Twenty-fourth Day of December, 2019

Andrei Iancu  
*Director of the United States Patent and Trademark Office*